United States Patent [19]

Naka et al.

[11] Patent Number: 4,992,437

[45] Date of Patent: Feb. 12, 1991

[54] THIENODIAZEPINE COMPOUNDS AND THEIR PHARMACEUTICAL USE

[75] Inventors: Yoichi Naka; Yukio Hitotsuyanagi; Keiichiro Haga, all of Nakatsu; Masahiro Hosoya, Tokorozawa, all of Japan

[73] Assignee: Yoshitomi Pharmaceutical Industries, Ltd., Osaka, Japan

[21] Appl. No.: 399,550

[22] PCT Filed: Dec. 16, 1988

[86] PCT No.: PCT/JP88/01278

§ 371 Date: Aug. 9, 1989

§ 102(e) Date: Aug. 9, 1989

[87] PCT Pub. No.: WO89/05812

PCT Pub. Date: Jun. 29, 1989

[30] Foreign Application Priority Data

Dec. 22, 1987 [JP]  Japan ................... 62-326465
Apr. 7, 1988 [JP]   Japan ................... 63-86960

[51] Int. Cl.⁵ ............. A61K 31/55; C07D 487/04; C07D 495/00
[52] U.S. Cl. .................. 514/220; 514/221; 540/497; 540/499; 540/503
[58] Field of Search .......... 540/499, 503, 497; 514/220, 221

[56] References Cited

U.S. PATENT DOCUMENTS 3,849,405 11/1974 Nakanishi et al. ............ 540/503
3,904,641 9/1975 Nakanishi et al. ............ 540/503

OTHER PUBLICATIONS

Evans et al., J. Med. Chem., 31, 1988, pp. 2235-2246.

Primary Examiner—Mukund J. Shah
Assistant Examiner—E. C. Ward
Attorney, Agent, or Firm—Wenderoth, Lind & Ponack

[57] ABSTRACT

Thienodiazepine compounds of the general formula

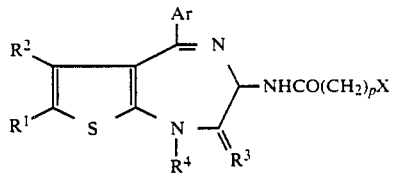

wherein $R^1$ and $R^2$ are the same or different and respectively stand for a hydrogen atom, a halogen, an alkyl or an aralkyl, or mean a group wherein $R^1$ and $R^2$ combinedly together form a ring; $R^3$ stands for an oxygen atom, $R^4$ stands for a hydrogen atom, an alkyl, an alkenyl or a group of the formula $-(CH_2)_m COOR^6$ (wherein $R^6$ stands for a hydrogen atom, an alkyl, an alkenyl or an aralkyl and m stands for an integer of 1-6), or $R^3$ and $R^4$ stand for a group wherein $R^3$ and $R^4$ combinedly together form a group of the formula $=N-N=C(R)^5-$ [wherein $R^5$ stands for a hydrogen atom, an alkyl, an alkenyl, an aralkyl or a group of the formula $-(CH_2)_n COOR^7$ wherein $R^7$ stands for a hydrogen atom, an alkyl, an alkenyl or an aralkyl and n stands for an integer of 1-6]; Ar and X are the same or different and respectively stand for an aryl or a heteroaryl; and p stands for an integer of 1-6, and their salts and their pharmaceutical use.

These compounds possess an antagonistic action to cholecystokinin and gastrin and exhibit a durable pancreatic enzymes- and gastric acid-secretion-suppressive action, and therefore are useful as the medicaments acting on the central nervous system and peripheral nervous system and as the prophylactic or therapeutic medicines for pancreatic disorders and gastrointestinal ulcers.

3 Claims, No Drawings

THIENODIAZEPINE COMPOUNDS AND THEIR PHARMACEUTICAL USE

TECHNICAL FIELD

This invention relates to thienodiazepine compounds and their salts which are novel and useful as medicaments, and to their pharmaceutical use.

BACKGROUND OF THE ART

In the specification of U.S. Pat. No. 3,849,405, it is disclosed that some kinds of thieno[2,3-e]-1,4-diazepine compounds possess central nervous actions such as an antidepressive action and an anticonvulsive action. In the specification of U.S. Pat. No. 3,904,641, it is disclosed that a certain kind of s-triazolo[3,4-c]thieno[2,3-e][1,4]diazepine compound has a useful pharmacological activity on the central nervous system such as an antidepressive activity and an anticonvulsive activity.

Meanwhile, as the substances which exist in the gastro-intestinal tissues and central nervous system and which are concerned with the control of the secretion of pancreatic enzymes and gastric acid, known are cholecystokinin (referred to also as CCK) which is a neuropeptide consisting of 33 amino acids and gastrin consisting of 34 amino acids. In connection with CCK, CCK-8 which consists of the 8 amino acids at the C terminus of CCK also possesses the same actions. Also, pentagastrin which consists of the 5 amino acids at the C terminus of gastrin possesses the same actions. The amino acid sequence of pentagastrin is identical with that at the C terminus of CCK.

Since the substances which exhibit an antagonistic action to these CCK and gastrin are effective in the prophylaxis and therapy of such diseases as pancreatic disorders and gastrointestinal ulcers, a number of such antagonistic substances have been studied so far. As an antagonistic substance to CCK, benzotripto is known [Proc. Natl. Acad. Sci. U.S.A., vol. 78, p. 6304 (1981)], and progulmide is known as an antagonistic substance to gastrin, [J. Med. Chem., vol. 27, p. 1597 (1984)]. Their actions are, however, relatively weak, and therefore, compounds having higher activities have been desired.

Besides, peptide antagonistic substances are not altogether satisfactory in that the durability of their actions is short and in that they are unstable and are not absorbed fully.

DISCLOSURE OF THE INVENTION

After the present inventors had conducted intensive studies for the purpose of creating substances which displayed effective antagonistic actions to CCK and gastrin and were useful as medicaments, they found a certain kind of thienodiazepine compound attained the purpose, which culminated in the completion of the present invention.

That is, this invention is to provide thienodiazepine compounds of the general formula

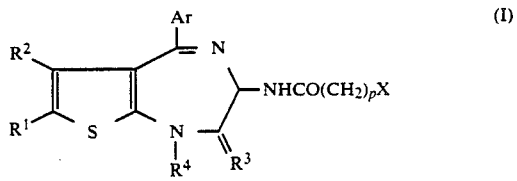

wherein $R^1$ and $R^2$ are the same or different and respectively stand for a hydrogen atom, a halogen, an alkyl or an aralkyl, or mean a group wherein $R^1$ and $R^2$ combinedly together form a ring; $R^3$ stands for an oxygen atom, $R^4$ stands for a hydrogen atom, an alkyl, an alkenyl or a group of the formula $-(CH_2)_mCOOR^6$ (wherein $R^6$ stands for a hydrogen atom, an alkyl, an alkenyl or an aralkyl and m stands for an integer of 1-6), or $R^3$ and $R^4$ stand for a group wherein $R^3$ and $R^4$ combinedly together form a group of the formula $=N-N=C(R^5)-$ [wherein $R^5$ stands for a hydrogen atom, an alkyl, an alkenyl, an aralkyl or a group of the formula $-(CH_2)_nCOOR^7$ (wherein $R^7$ stands for a hydrogen atom, an alkyl, an alkenyl or an aralkyl and n stands for an integer of 1-6)]; Ar and X are the same or different and respectively stand for an aryl or a heteroaryl; and p stands for an integer of 1-6, or their salts.

Also, the present invention is to provide pharmaceutical compositions containing a thienodiazepine compound of the above-mentioned general formula (I) or a salt thereof.

In the foregoing definition and the present specification, the halogen means chlorine, bromine, fluorine or iodine; the alkyl means an alkyl having 1-20 carbon atoms such as methyl, ethyl, propyl, isopropyl, butyl, isobutyl, tertbutyl, pentyl, isopentyl, tert-pentyl, hexyl, octyl, 2-ethylhexyl, 1,1,3,3-tetramethylbutyl, nonyl, decyl, dodecyl, tetradecyl, octadecyl or eicosyl; the alkenyl means an alkenyl having 2 to 8 carbon atoms such as vinyl, 1-propenyl, allyl, isopropenyl, 2-butenyl, 2-pentenyl, 3-hexenyl or 6-octenyl; the alkoxy means an alkoxy having 1-20 carbon atoms such as methoxy, ethoxy, propoxy, isopropoxy, butoxy, isobutoxy, tert-butoxy, pentyloxy, hexyloxy, octyloxy, decyloxy, dodecyloxy, octadecyloxy or eicosyloxy; the aralkyl means a benzyl, 1-phenylethyl, 2-phenylethyl, 3-phenylpropyl, 4-phenylbutyl, 1-naphthylmethyl, 2-naphthylmethyl or the like which may have, on the aromatic ring, one to three substituent(s) selected from among halogens, alkyls, alkoxys, trifluoromethyl, nitro, amino, cyano and hydroxy group; the aryl means a phenyl, a 1-naphthyl, a 2-naphthyl or the like which may have, on the aromatic ring, 1-3 substituent(s) selected from among halogens, alkyls, alkoxys, trifluoromethyl, nitro, amino, cyano and hydroxy group; the heteroaryl means a pyridyl (2-pyridyl, 3-pyridyl, 4-pyridyl), a quinolyl (e.g. 2-quinolyl, 3-quinolyl), an indolyl (e.g. 2-indolyl, 3-indolyl), a thienyl (2-thienyl, 3-thienyl), a furyl (2-furyl, 3-furyl), a benzofuranyl (e.g. 2-benzofuranyl, 3-benzofuranyl), a 1H-benzimidazol-2-yl, a 2-benzothiazolyl or the like which may have, on the ring, one to three substituent(s) selected from among halogens, alkyls, alkoxys, trifluoromethyl, nitro, amino, cyano and hydroxy group; the ring formed combinedly together by $R^1$ and $R^2$ means a cyclopentene ring, a cyclopentadiene ring, a cyclohexene ring, a cyclohexadiene ring, a benzene ring, a cycloheptene ring, a cycloheptadiene ring, a cycloheptatriene or the like.

As the salts of the compounds of the general formula (I), mention can be made of acid addition salts with inorganic acids or organic acids and salts with inorganic bases, organic bases or amino acids. From the purposes of the present invention, nontoxic salts are preferable.

Since the compounds of the general formula (I) have at least one chiral carbon atom, they can exist as a racemic body, an optically active isomer or a diastereomer, all of which are encompassed in the present invention.

The compounds of the general formula (I) of the present invention can be produced by reacting a compound of the general formula

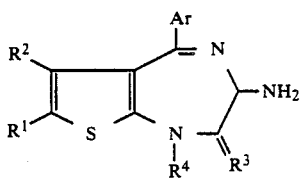
(II)

wherein each of the symbols is as defined above with a compound of the general formula

X—CO—Z (III)

wherein X is as defined above and Z stands for a leaving group [hydroxy group, a halogen, an ester residue (e.g. pentachlorophenoxy, p-nitrophenoxy), a thioester residue (e.g. phenylthio, 2,6-dimethylpyridine-4-thio), etc.].

The reaction usually proceeds in a solvent inert to the reaction (water, methanol, ethanol, tetrahydrofuran, diethyl ether, dioxane, dichloromethane, chloroform, ethyl acetate, benzene, toluene, dimethylformamide, dimethylacetamide, acetic acid, etc. or a mixed solvent thereof) at a temperature ranging from about $-20°$ C. to the boiling point of the solvent used, in the presence of a base or a dehydrating-condensing agent if necessary, for about 30 minutes to 24 hours.

As the base to be used as necessary, mention is made of alkali metal hydroxides (sodium hydroxide, potassium hydroxide, etc.), alkali metal carbonates (sodium carbonate, potassium carbonate, etc.), alkali metal hydrogencarbonate (sodium hydrogencarbonate, potassium hydrogencarbonate, etc.), alkali metal hydrides (sodium hydride, etc.), and organic bases (triethylamine, pyridine, picoline, N-methylmorpholine, etc.). The reaction can be conducted by using a phase transfer catalyst such as tetrabutylammonium bromide or benzyltriethylammonium iodide and an alkali metal hydroxide in a two-phase solvent consisting of an organic solvent mentioned above and water. As the dehydrating-condensing agent, preferred are dehydrating-condensing agents usable for amide synthesis, which are exemplified by dicyclohexylcarbodiimide, N-methyl-2-chloropyridinium iodide, molecular sieve and the like.

The compounds of the formula (I) wherein $R^3$ and $R^4$ combinedly form a group of the formula forming =N—N=C($R^5$)— can be produced by reacting a compound (I) wherein $R^3$ is an oxygen and $R^4$ is a hydrogen atom representable by the formula

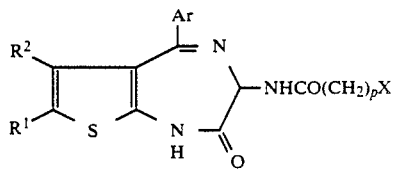
(IV)

wherein each of the symbols is as defined above with a thionation reagent to obtain a compound of the general formula

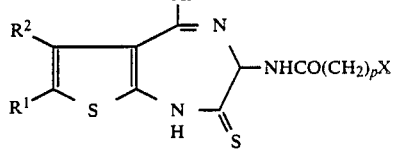
(V)

wherein each of the symbols is as defined above, followed by the reaction of this compound of the general formula (V) with a compound of the general formula $R^5$CONHNH$_2$ (VI)

, or alternatively by the reaction of the compound of the general formula (V) with hydrazine hydrate to obtain a compound of the general formula

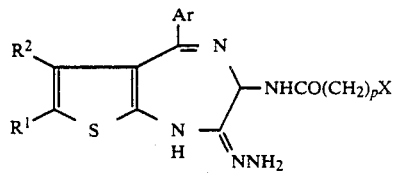
(VII)

wherein each of the symbols is as defined above, followed by the reaction of the compound (VII) with a compound of the general formula $R^5$COOH (VIII)

wherein $R^5$ is as defined above or its reactive derivative or with a compound of the general formula $R^5$C(OR$^8$)$_3$ (IX)

wherein $R^8$ stands for an alkyl such as methyl or ethyl and $R^5$ is as defined above.

As the thionation reagent to be used for the above-mentioned method, mention is made of phosphorus pentasulfide, Lowesson reagent [2,4-bis(4-methoxyphenyl)-1,3,2,4-diphosphetane-2,4-disulfide] and the like. As the reactive derivatives of the compounds of the general formula (VIII), mention is made of acid halides, acid anhydrides mixed acid anhydrides, $C_{1-5}$ alkyl esters, benzylesters and so on.

The reaction of a compound of the general formula (IV) with a thionation reagent usually proceeds in a solvent inert to the reaction (pyridine, dimethylaniline, benzene, toluene, xylene, tetrahydrofuran, chloroform, dioxane, etc. or a mixed solvent thereof) at a temperature ranging from 30° C. to 100° C. for 30 minutes to 5 hours.

The reaction of a compound of the general formula (V) with a compound of the general formula (VI) usually proceeds in a solvent inert to the reaction (benzene, toluene, xylene, tetrahydrofuran, dioxane, etc. or a mixed solvent thereof in the presence of an organic acid (acetic acid, propionic acid etc.), an inorganic acid (hydrochloric acid, sulfuric acid etc.) or silica gel at a temperature ranging from room temperature to the refluxing temperature of the solvent used for 30 minutes to 5 hours.

The reaction of a compound of the general formula (V) with hydrazine hydrate usually proceeds in a solvent inert to the reaction (methanol, ethanol, propanol, isopropyl alcohol, butanol, etc.) at a temperature ranging from 0° C. to 40° C. for about 5 minutes to about 3 hours.

The reaction of a compound of the general formula (VII) with a compound of the general formula (VIII) or its reactive derivative or a compound of the general formula (IX) proceeds in a solvent inert to the reaction (benzene, toluene, xylene, tetrahydrofuran, dioxane, etc. or a mixed solvent thereof) in the presence of an organic acid (acetic acid, propionic acid, etc.), an inorganic acid (hydrochloric acid, sulfuric acid, etc.) or silica gel at a temperature ranging from room temperature to the refluxing temperature of the solvent used for 30 minutes to 6 hours.

The thus obtained compounds of the general formula (I) can be separated from the reaction mixture and purified by the per se known methods such as recrystallization and chromatography.

The compounds of the general formula (I) can be converted into their salts by the treatment with an inorganic acid (hydrochloric acid, hydrobromic acid, sulfuric acid, phosphoric acid, nitric acid, etc.), an organic acid (acetic acid, propionic acid, succinic acid, glycolic acid, lactic acid, malic acid, tataric acid, citric acid, maleic acid, fumaric acid, methanesulfonic acid, p-toluenesulfonic acid, ascorbic acid, etc.), an inorganic base (sodium hydroxide, potassium hydroxide, calcium hydroxide, magnesium hydroxide, zinc hydroxide, ammonium hydroxide, etc.), an organic base (methylamine, diethylamine, triethylamine, dicyclohexylamine, triethanolamine, ethylenediamine, trishydroxymethylaminomethane, quinine, cinchonine, etc.) or an amino acid (lysine, ornithine, arginine, guanidine).

Among the compounds of the present invention, those having a chiral carbon can be usually obtained as racemic bodies. The racemic bodies can be resolved into their optical isomers. These optical isomers can also be produced by using the optically active starting compounds. The individual diastereomers can be purified by preparative recrystallization or chromatography.

The compounds encompassed in the present invention are exemplified by the following.

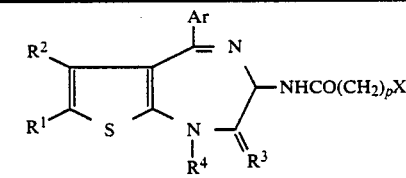

| Ar | R¹ | R² | R³ | R⁴ | X | p | m.p. (°C.) |
|---|---|---|---|---|---|---|---|
| 2-ClPh | Et | H | =N—N=C(Me)— | | 2-Indolyl | 0 | 284~286 (d) |
| 2-ClPh | Et | H | =N—N=C(Me)— | | 3-Indolyl | 1 | 259 |
| 2-ClPh | Et | H | =N—N=C(Pr)— | | 2-Indolyl | 0 | 265~266 |
| 2-ClPh | Et | H | =N—N=C(Pr)— | | 2-Naphthyl | 0 | 226~227 |
| 2-ClPh | Et | H | O | Me | 2-Indolyl | 0 | 257~259 (d) |
| 2-ClPh | Et | H | O | Me | 3,4-diClPh | 0 | 180~181 |
| 2-ClPh | Et | H | =N—N=C(Me)— | | 2-Naphthyl | 0 | |
| 2-NO₂Ph | Et | H | =N—N=C(Me)— | | 2-Indolyl | 0 | |
| 4-MePh | Et | H | =N—N=C(Me)— | | 2-Indolyl | 0 | |
| 2-ClPh | Et | H | =N—N=CH— | | 2-Indolyl | 0 | 287~288 (d) |
| Ph | Et | H | =N—N=C(Me)— | | 2-Indolyl | 0 | |
| 2-ClPh | Me | Me | =N—N=C(Me)— | | 2-Indolyl | 0 | |
| 2-ClPh | —(CH₂)₄— | | =N—N=C(Me)— | | 2-Indolyl | 0 | 304~306 (d) |
| Ph | H | H | =N—N=C(Me)— | | 2-Indolyl | 0 | |
| 2-ClPh | Me | Me | O | Me | 2-Indolyl | 0 | |
| 2-ClPh | —(CH₂)₄— | | O | Me | 2-Indolyl | 0 | |
| 4-MeOPh | Me | Me | =N—N=C(Me)— | | 2-Indolyl | 0 | |
| 2-ClPh | Et | H | =N—N=CH— | | 2-Naphthyl | 0 | |
| 2-ClPh | Me | Me | =N—N=C(Me)— | | 2-Indolyl | 0 | |
| Ph | Cl | H | =N—N=C(Me)— | | 2-Indolyl | 0 | |
| Ph | Et | H | O | CH₂COOH | 2-Indolyl | 0 | |
| 2-MeOPh | Et | H | =N—N=C(Me)— | | 2-Indolyl | 0 | |
| 2,4-diClPh | Et | H | =N—N=C(Me)— | | 2-Indolyl | 0 | |
| 3,4-diClPh | Et | H | =N—N=C(Me)— | | 2-Indolyl | 0 | |
| 3-Py | Et | H | =N—N=C(Me)— | | 2-Indolyl | 0 | |
| 2-ClPh | Et | H | =N—N=C(Me)— | | 2-Thienyl | 0 | |
| 2-ClPh | Et | H | =N—N=C(Me)— | | 2-Pyridyl | 0 | |
| 2-ClPh | Et | H | =N—N=C(Me)— | | 2-Benzimidazolyl | 0 | |
| 2-ClPh | Et | H | =N—N=C(Me)— | | 2-Benzofuranyl | 0 | |
| 2-ClPh | Et | H | =N—N=C(Me)— | | 2-Benzothiazolyl | 0 | |
| 2-ClPh | Et | H | =N—N=C(Me)— | | 3,4-diClPh | 0 | 254~255 |

In Table, Cl means chlorine, Et means ethyl, Me means methyl, MeO means methoxy, NO₂ means nitro, Ph means phenyl, Pr means propyl, Py means pyridyl and (d) means decomposition point.

The starting compounds of the general formula (II) are novel and can be produced, for example, in the following manner.

By reacting a compound of the general formula

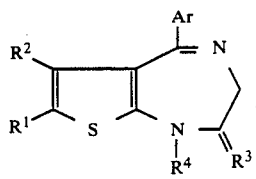

wherein each of the symbols is as defined above with a dialkyl carbonate (e.g. diethyl carbonate) in the presence of a base (sodium hydride, potassium tert-butoxide, etc.), an alkoxycarbonyl group (ethoxycarbonyl, etc.) is introduced at the 6-position of the compound (X), and the thus-obtained compound is reacted with a 0-(2,4-dinitrophenyl)hydroxylamine to give a compound of the general formula

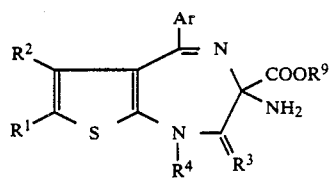

wherein $R^9$ stands for an alkyl and the other symbols are as defined above and the thus-obtained compound of the general formula (XI) is subjected to hydrolysis in the presence of a base (e.g. sodium hydroxide, potassium hydroxide, barium hydroxide) in water or a mixture of water and an organic solvent (preferably, methanol, ethanol, diethyl ether, tetrahydrofuran, dioxane, etc.) at a temperature ranging from about 0° C. to the boiling point of the solvent used to give the reaction mixture, which is rendered acidic with the use of an acid such as hydrochloric acid, hydrobromic acid, hydrofluoric acid, sulfuric acid, trifluoroacetic acid or trifluoromethanesulfonic acid to give a compound of the general formula (II).

Since the compounds of the present invention and their salts possess excellent antagonistic actions to cholestokinin and gastrin and potent and durable pancreatic enzyme- and gastric acid-secretion-suppressive actions, they are useful as the medicaments acting on the central nervous and peripheral nervous systems and the prophylactic and therapeutic medicines for pancreatic disorders and gastrointestinal ulcers.

Below, shown are the pharmacological actions of the compound of the present invention.

The compound of the present invention used for the test is as follows:

Compound A: 4-(2-Chlorophenyl)-2-ethyl-6-(2-indolecarboxamido)-9-methyl-6H-thieno[3,2-f][1,2,4]triazolo[4,3-a][1,4]diazepine Also as the control compounds, there were used CCK-8, CCK-4 and the following compound.

L-364718: N-(2,3-Dihydro-1-methyl-2-oxo-5-phenyl-1H-1,4-benzodiazepin-3-yl)-1H-indole-2-carboxamide

EXPERIMENTAL EXAMPLE 1

Effects on gastric excreting capability (Gastric emptying test)

The solutions of the test compounds were orally administered to male ddY mice weighing about 20 g, and 25 minutes after the oral adminstration, CCK-8 was subcutaneously administered at the dose of 30 μg/kg. At 5 minutes' lapse thereafter, 0.1 ml of a 1.5% aqueous solution of methyl cellulose containing 0.05% phenolred (Sigma) was orally administered. After 15 minutes, the stomach was extracted and the gastric contents were mixed with a 10% aqueous solution of trichloroacetic acid. After the removal of the proteins, the residue was centrifuged at 3000 rpm for 10 minutes. To the supernatant was added a 1N solution of sodium hydroxide and the mixture was again centrifuged. Thereafter, $OD_{560}$ value of the supernatant was measured by the spectrophotometer (Hitachi 200-10 type) to estimate the minimum effective dose (MED).

The results are tabulated in Table 1.

EXPERIMENTAL EXAMPLE 2

CCK receptor-binding

The entire pancreas of a male mongrel adult dog was extracted and the fat tissues thereof were removed. The residual portion was homogenized in 50 mM tris hydrochloride (pH 7.5) (Blinkman·Polytron PT20). After the filtration with nylon cloth (120 mesh) followed by centrifugation (50,000×g, for 12 minutes), the obtained sediment was homogenized in a tris buffer solution in the same manner as mentioned above and the homogenate was centrifuged. The obtained sediment was suspended in a buffer solution for binding assay (5 mM magnesium chloride, chloride, 5 mM dithiothreitol, 2 mg/ml bovine serum albumin, 0.1 mg/ml bacitracin, and 50 mM tris hydrochloride, pH 7.2), containing 0.14 mg/ml trypsin-inhibitor (soy bean), and the suspension was used as the receptor source.

The binding assay was conducted by adding 50 μl of buffer solution (for the entire binding), unmarked CCK-8 sulfate (for the non-specific binding) or test compound (for the measurement of binding-inhibitory capability of $^{125}I$-CCK) of the final concentration of 1 μM and 50 μl of $^{125}I$-CCK-8 (63-67 TBq/mmol, 40,000-50,000 cpm) to 450 μl of membrane suspension (containing 100 μg of proteins), incubating the reaction mixture at 20° C. for 30 minutes, suction-filtering the mixture with glass fibre filter paper (Whatmann G/FB), washing three times with 2.5 ml per each tube of an ice-cooled tris buffer solution immediately after the suction-filtration and measuring the radio activity concentration on the filter paper.

The effect of the test compound on binding to CCK receptor was estimated by the concentration at which the specific binding is 50% suppressed ($IC_{50}$, nM) based on the inhibitory rate calculated in accordance with the following formula.

$$\text{Inhibitory rate} = \frac{\text{Binding when Compound added} - \text{Non-specific binding}}{\text{The entire binding} - \text{Non-specific binding}} \times 100 \, (\%)$$

The results are tabulated in Table 1.

TABLE 1

| Test Compound | Gastric Emptying MED (mg/kg p.o.) | CCK binding, $IC_{50}$ (nM) Pancreas | Brain |
|---|---|---|---|
| A | 0.3–1.0 | 0.60 | 1.80 |
| L-364718 | 0.1–0.3 | 0.60 | 85.00 |
| CCK-8 | — | 0.60 | 0.50 |
| CCK-4 | — | 800.00 | 83.00 |

EXPERIMENTAL EXAMPLE 3

Acute toxicity test

The acute toxicity of the compounds of the present invention was studied with the use of 6 male mice. After the test Compound A was orally administered to the mice and the mice were observed for consecutive 5 days, it was found that the Compound A had low toxicity.

When the compounds of the present invention and their pharmaceutically acceptable salts are used as medicaments, they are usually admixed with pharmaceutically acceptable additives such as carriers, excipients, diluents and solubilizing agents (lactose, corn starch, talc, kaolin, physiological saline, sterilized water etc.) and safely administered to patients in forms such as tablets (including sugar-coated tablets and film-coated tablets), capsules, powders, injections, instillations, suppositories and cataplasms.

While the dosage varie depending upon the sex difference, age, body-weight, symptom and so on of patients, the preferable daily dosage for oral administration, is usually in the range from about 1 to about 500 mg per adult man.

The present invention is specifically explained by working examples and examples for the preparation of starting compounds, to which the present invention is, needless to say, not limited.

Starting Compound-Preparation Example 1

To 500 ml of diethyl carbonate were added 22.0 g of 4-(2-chlorophenyl)-2-ethyl-9-methyl-6H-thieno[3,2-f][1,2,4]-triazolo[4,3-a][1,4]diazepine and 4.3 g of sodium hydride, and the mixture was heated. Hydrogen gas began to generate at about 100° C., while the solution gradually colored violet. After 30 minutes' reflux, the mixture was cooled to 20° C., whereto 16.0 g of O-(2,4-dinitrophenyl)hydroxylamine was added. The mixture was stirred for 2 hours. After the completion of the reaction, the reaction mixture was poured into ice-water containing 6 ml of acetic acid. The diethyl carbonate layer was separated, washed twice with water and dried over anhydrous magnesium sulfate. Diethyl carbonate was distilled off under reduced pressure, and diisopropyl ether was added to the obtained residue to separate crystals, which were collected by filtration. The crystals were recrystallized from ethyl acetate to give 18.2 g of ethyl 6-amino-4-(2-chlorophenyl)-2-ethyl-9-methyl-6H-thieno[3,2-f][1,2,4]-triazolo[4,3-a][1,4]diazepine-6-carboxylate, m.p. 180°–181° C.

In a mixture of 180 ml of ethanol and 60 ml of water was dissolved 15.1 g of ethyl 6-amino-4-(2-chlorophenyl)-2-ethyl-9-methyl-6H-thieno[3,2-f][1,2,4]triazolo[4,3-a][1,4]diazepine-6-carboxylate. To the solution was added 6.0 g of crystals of barium hydroxide·8 hydrate, and the mixture was stirred at room temperature for 24 hours. After the solvent was distilled off under reduced pressure, 200 ml of water and 100 ml of benzene were added and the mixture was stirred fully. The water layer was separated, adjusted to pH 2 with 1N hydrochloric acid and left standing still for 24 hours. Thereafter, the mixture was neutralized with sodium carbonate, and the precipitated crystals were collected by filtration. The obtained crystals were dissolved in chloroform and insoluble matters were filtered off. After the solvent was distilled off under reduced pressure, the residue was recrystallized from ethanol to give 10.7 g of 6-amino-4-(2-chlorophenyl)-2-ethyl-9-methyl-6H-thieno[3,2-f][1,2,4]triazolo[4,3-a][1,4]-diazepine, m.p. 130°–131° C.

EXAMPLE 1

To 120 ml of tetrahydrofuran were added 5.0 g of 6-amino-4-(2-chlorophenyl)-2-ethyl-9-methyl-6H-thieno[3,2-f][1,2,4]triazolo[4,3-a][1,4]diazepine, 2.7 g of indole-2-carboxylic acid, 4.3 g of 2-chloro-N-methyl pyridinium iodide and 6.2 g of dibutyl amine, and the mixture was heated under reflux while stirring for 90 minutes. After the solvent was distilled off under reduced pressure, the residue was washed with diisopropyl ether. Ethanol was added to separate crystals, which were collected by filtration. The thus-obtained crystals were recrystallized from chloroform-ethanol to give 4.9 g of 4-(2-chlorophenyl)-2-ethyl-6-(2-indolecarboxamido)-9-methyl-6H-thieno[3,2-f][1,2,4]triazolo[4,3-a][1,4]diazepine, m.p. 284°–286° C. (decomposition).

EXAMPLE 2

In 20 ml of chloroform was dissolved 1.5 g of 6-amino-4-(2-chlorophenyl)-2-ethyl-9-propyl-6H-thieno[3,2-f][1,2,4]-triazolo[4,3-a][1,4]diazepine, and 0.47 g of triethylamine was added to the solution. A solution of 0.89 g of naphthalene-2-carbonyl chloride in 10 ml of chloroform was added dropwise to the mixture at not more than 10° C. The mixture was further stirred for 1 hour at room temperature and washed with 0.1N hydrochloric acid, 0.1N sodium hydroxide and a saturated solution of sodium chloride in order. Thereafter, the solvent was distilled off under reduced pressure, and the residue was washed with diisopropyl ether. Ethanol was added to yield crystals, which were collected by filtration. The crystals were recrystallized from chloroform-ethanol to give 1.4 g of 4-(2-chlorophenyl)-2-ethyl-6-(2-naphthalenecarboxamido)-9-propyl-6H-thieno[3,2-f][1,2,4]triazolo[4,3-a][1,4]diazepine, m.p. 226°–227° C.

EXAMPLE 3

By following the procedure in Example 1 with the use of 6-amino-4-(2-chlorophenyl)-2-ethyl-9-propyl-6H-thieno[3,2-f][1,2,4]triazolo[4,3-a][1,4]diazepine and indole-2-carboxylic acid, obtained was 4-(2-chlorophenyl)-2-ethyl-6-(2-indolecarboxamido)-9-propyl-6H-thieno[3,2-f][1,2,4]triazolo[4,3-a][1,4]diazepine, m.p. 265°–266° C.

EXAMPLE 4

In the same manner as in Example 1 with the use of 6-amino-4-(2-chlorophenyl)-2-ethyl-9-methyl-6H-thieno[3,2-f][1,2,4]triazolo[4,3-a][1,4]diazepine and indole-3-acetic acid, obtained was 4-(2-chlorophenyl)-2-ethyl-6-(3-indoleactamido)-9-methyl-6H-thieno[3,2-f][1,2,4]triazolo[4,3-a][1,4]diazepine, m.p. 259° C.

EXAMPLE 5

By following the procedure in Example 1 with 6-amino-4-(2-chlorophenyl)-2-ethyl-8-methyl-8H-6,7-dihydro-thieno[3,2-f][1,4]diazepin-7-one and indole-2-carboxylic acid, obtained was 4-(2-chlorophenyl)-2-ethyl-6-(2-indolecarboxamido)-8-methyl-8H-6,7-dihydro-thieno[3,2-f][1,4]diazepin-7-one, m.p. 257°–259° C. (decomposition).

EXAMPLE 6

By following the procedure in Example 2 with 6-amino-4-(2-chlorophenyl)-2-ethyl-8-methyl-8H-6,7-dihydro-thieno[3,2-f][1,4]diazepine and 3,4-dichlorobenzoyl chloride, obtained was 4-(2-chlorophenyl)-2-ethyl-6-(3,4-dichlorobenzoylamino)-8-methyl-8H-6,7-dihydro-thieno[3,2-f][1,4]diazepin-7-one, m.p. 180°–181° C.

While the present invention has been described by the foregoing specification including working examples, the embodiment described herein can be changed and modified in various manners within the scope and the spirit of the present invention.

We claim:

1. A thienodiazepine compound of the general formula

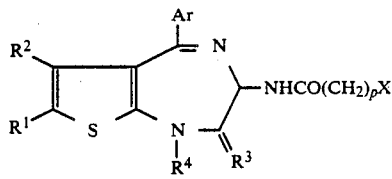

wherein $R^1$ and $R^2$ are the same or different and respectively represent a hydrogen, a halogen, a $C_{1-20}$ alkyl or an aralkyl selected from the group consisting of benzyl, 1-phenylethyl, 2-phenylethyl, 3-phenylpropyl, 4-phenylbutyl, 1-naphthylmethyl and 2-naphthylmethyl unsubstituted or substituted on the aromatic ring by one to three substituent(s) selected from the group consisting of halogen, alkyl, alkoxy, trifluoromethyl, nitro, amino, cyano and hydroxy, or wherein $R^1$ and $R^2$ together form a ring selected from the group consisting of a cyclopentene ring, a cyclopentadiene ring, a cyclohexene ring, a cyclohexadiene ring, a benzene ring, a cycloheptene ring, a cycloheptadiene ring and a cycloheptatriene ring; $R^3$ represents an oxygen, $R^4$ represent a hydrogen, a $C_{1-20}$ alkyl, a $C_{2-8}$ alkenyl or a group of the formula —$(CH_2)_m COOR^6$ (wherein $R^6$ represents a hydrogen atom, a $C_{1-20}$ alkyl, a $C_{2-8}$ alkenyl or an aralkyl selected from the group consisting of benzyl, 1-phenylethyl, 2-phenylethyl, 3-phenylpropyl, 4-phenylbutyl, 1-naphthylmethyl and 2-naphthylmethyl unsubstituted or substituted on the aromatic ring by one to three substituent(s) selected from the group consisting of halogen, alkyl, alkoxy, trifluoromethyl, nitro, amino, cyano and hydroxy, and m represents an integer of 1-6), or $R^3$ and $R^4$ together form a group of the formula =N—N=C($R^5$)—, wherein $R^5$ represents a hydrogen, a $C_{1-20}$ alkyl, a $C_{2-8}$ alkenyl, an aralkyl selected from the group consisting of benzyl, 1-phenylethyl, 2-phenylethyl, 3-phenylpropyl, 4-phenylbutyl, 1-naphthylmethyl and 2-naphthylmethyl unsubstituted or substituted on the aromatic ring by one to three substituent(s) selected from the group consisting of halogen, alkyl, alkoxy, trifluoromethyl, nitro, amino, cyano and hydroxy, or a group of the formula —$(CH_2)_n COOR^7$ (wherein $R^7$ represents a hydrogen, a $C_{1-20}$ alkyl, a $C_{2-8}$ alkenyl or an aralkyl selected from the group consisting of benzyl, 1-phenylethyl, 2-phenylethyl, 3-phenylpropyl, 4-phenylbutyl, 1-naphthylmethyl and 2-naphthylmethyl unsubstituted or substituted on the aromatic ring by one to three substituent(s) selected from the group consisting of halogen, alkyl, alkoxy, trifluoromethyl, nitro, amino, cyano and hydroxy, and n represents an integer of 1-6); Ar and X are the same or different and respectively represent an aryl selected from the group consisting of a phenyl, a phenyl substituted by 1 or 2 substituents selected from the group consisting of halogen, alkyl, alkoxy and nitro, and a 2-naphthyl or a heteroaryl selected from the group consisting of a pyridyl, an indolyl, a thienyl, a benzofuranyl, a 1H-benzimidazol-2-yl and a 2-benzothiazolyl; and p represents an integer of 1-6, or its salt.

2. A compound as claimed in claim 1 which is selected from a group consisting of the following compounds:

4-(2-chlorophenyl)-2-ethyl-6-(2-indolecarboxamido)-9-methyl-6H-thieno[3,2-f][1,2,4]triazolo[4,3-a][1,4]diazepine, 4-(2-chlorophenyl)-2-ethyl-6-(2-naphthalenecarboxamido)-9-propyl-6H-thieno[3,2-f][1,2,4]triazolo[4,3-a][1,4]diazepine, 4-(2-chlorophenyl)-2-ethyl-6-(2-indolecarboxamido)-9-propyl-6H-thieno[3,2-f][1,2,4]triazolo[4,3-a][1,4]diazepine, 4-(2-chlorophenyl)-2-ethyl-6-(3-indoleacetamido)-9-methyl-6H-thieno[3,2-f][1,2,4]triazolo[4,3-a][1,4]diazepine, 4-(2-chlorophenyl)-2-ethyl-6-(2-indolecarboxamido)-8-methyl-8H-6,7-dihydro-thieno[3,2-f][1,4]diazepin-7-one 4-(2-chlorophenyl)-2-ethyl-6-(3,4-dichlorobenzoylamino)-8-methyl-8H-6,7-dihydro-thieno[3,2-f][1,4]diazepin-7-one, 4-(2-chlorophenyl)-2-ethyl-6-(2-indolecarboxamido)-6H-thieno-[3,2-f][1,2,4]triazolo[4,3-a][1,4]diazepine, 6-(2-chlorophenyl)-7,8,9,10-tetrahydro-4-(2-indolecarboxamido)-1-methyl-4H-(1)benzothieno[3,2-f][1,2,4]triazolo[4,3-a][1,4]-diazepine and 4-(2-chlorophenyl)-2-ethyl-6-(3,4-dichlorobenzoylamino)-9-methyl-6H-thieno[3,2-f][1,2,4]triazolo[4,3-a][1,4]diazepine.

3. A pharmaceutical composition which comprises a therapeutically effective amount of a compound as claimed in claim 1 and a pharmaceutically acceptable additive.

* * * * *